US006495143B2

(12) United States Patent
Lee et al.

(10) Patent No.: US 6,495,143 B2
(45) Date of Patent: *Dec. 17, 2002

(54) BOTULINUM NEUROTOXIN VACCINE

(75) Inventors: John S. Lee, Hagerstown, MD (US); Peter Pushko, Frederick, MD (US); Jonathan F. Smith, Sabillasville, MD (US); Michael Parker, Frederick, MD (US); Mark T. Dertzbaugh, Fairfield, PA (US); Leonard Smith, Clarksburg, MD (US)

(73) Assignee: The United States of America as represented by the Secretary of the Army, Washington, DC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/350,756

(22) Filed: Jul. 9, 1999

(65) Prior Publication Data

US 2002/0034521 A1 Mar. 21, 2002

Related U.S. Application Data

(63) Continuation-in-part of application No. 08/981,159, filed as application No. PCT/US96/07454 on May 21, 1996, which is a continuation-in-part of application No. 08/448,630, filed on May 23, 1995, now Pat. No. 5,792,462.
(60) Provisional application No. 60/092,416, filed on Jul. 10, 1998, and provisional application No. 60/133,870, filed on May 12, 1999.

(51) Int. Cl.[7] .................... C12N 15/86; C12N 7/01; C12N 5/10; A61K 39/08; A61K 39/295
(52) U.S. Cl. ............... 424/199.1; 424/201.1; 424/247.1; 435/69.1; 435/69.3; 435/320.1; 435/235.1; 435/325; 435/252.3; 514/44
(58) Field of Search ................ 435/320.1, 235.1, 435/325, 252.3, 69.3, 69.1; 536/23.72; 424/199.1, 201.1, 247.1; 514/44

(56) References Cited

U.S. PATENT DOCUMENTS

| 5,792,462 A | * | 8/1998 | Johnston et al. ......... 424/199.1 |
| 5,814,482 A | * | 9/1998 | Dubensky, Jr. et al. .... 435/69.3 |
| 5,919,665 A | * | 7/1999 | Williams ................. 435/71.1 |
| 5,939,070 A | * | 8/1999 | Johnson et al. .......... 424/194.1 |

FOREIGN PATENT DOCUMENTS

| WO | WO 96/37616 | 11/1996 |
| WO | WO 98/08540 | 3/1998 |

OTHER PUBLICATIONS

Oguma et al. Microbiol. Immunol. 39(3) 161–168, 1995.*
PCT International Search Report for international patent application PCT/US99/15570 (corresponding to US application Ser. No. 09/350,756), dated Jun. 26, 2000 (6 pages).
Anderson et al., "Immune Response in Mice following Immunization with DNA Encoding Fragment C of Tetanus Toxin", Infection and Immunity, vol. 64, No. 8, document No. XP–002139492, Aug. 1996, pp. 3168–3173.
Pushko, et al., "Replicon–Helper Systems from Attenuated Venezuelan Equine Encephalitis Virus: Expression of Heterologous Genes in Vitro and Immunization against Heterologous Pathogens in Vivo," Virology:239, pp. 389–401 (1997), document No. XP–0021399493.
Clayton et al., "Protective Vaccination with a Recombinant Fragment of Clostridium botulinum Neurotoxin Serotype A Expressed from a Synthetic Gene in *E. coli*", Infection and Immunity, Jul. 1995, vol. 63, No. 7, pp. 2738–2742.
Byrne, et al., "Purification, Potency, and Efficacy of the Botulinum Neurotoxin Type A Binding Domain from Pichia pastoris as a Recombinant Vaccine Candidate", Infection and Immunity, Oct. 1998, vol. 66, No. 10, pp. 4817–4822.
Pushko, et al., "Replicon–Helper Systems from Attenuated Venezuelan Equine Encephalitis Virus: Expression of Heterologous Genes in Vitro and Immunization against Heterologous Pathogens in Vivo," Virology:239, pp. 389–401 (1997).
Bavari, et al., "Engineered Bacterial Superantigen Vaccines", Vaccines 96, 1996, pp. 135–141.
Welkos et al., "Sequence and analysis of the DNA encoding protective antigen of Bacillus anthracis", Gene, 69, 1988, pp. 287–300.

* cited by examiner

*Primary Examiner*—Mary E. Mosher
(74) *Attorney, Agent, or Firm*—Elizabeth Arwine; Charles M. Harris

(57) ABSTRACT

Using the nontoxic heavy chain fragment from botulinum neurotoxins A–G, compositions and methods of use in inducing an immune response which is protective against intoxication with botulinum in subjects is described.

28 Claims, 5 Drawing Sheets

FIG. 1

Botulinum Neurotoxin Hc Fragment

| kDa | lysate[a] | STD[b] |
|---|---|---|
| 66.2 | | |
| 39.2 | ▬ | ▬ |

SEQUENCE LISTING

<160> NUMBER OF SEQ ID NOS: 11

<210> SEQ ID NO 1
<211> LENGTH: 1338
<212> TYPE: DNA
<213> ORGANISM: Artificial
<220> FEATURE:
<223> OTHER INFORMATION: /note="synthetic sequence encoding botulinum neurotoxin"

<400> SEQUENCE: 1

```
gtcgagccat ggctcgtctg ctgtctacct tcactgaata            40
catcaagaac atcatcaata cctccatcct gaacctgcgc            80
tacgaatcca atcacctgat cgacctgtct cgctacgctt           120
ccaaaatcaa catcggttct aaagttaact tcgatccgat           160
cgacaagaat cagatccagc tgttcaatct ggaatcttcc           200
aaaatcgaag ttatcctgaa gaatgctatc gtatacaact           240
ctatgtacga aaacttctcc acctccttct ggatccgtat           280
cccgaaatac ttcaactcca tctctctgaa caatgaatac           320
accatcatca actgcatgga aaacaattct ggttggaaag           360
```

-continued

| | |
|---|---|
| tatctctgaa ctacggtgaa atcatctgga ctctgcagga | 400 |
| cactcaggaa atcaaacagc gtgttgtatt caaatactct | 440 |
| cagatgatca acatctctga ctacatcaat cgctggatct | 480 |
| tcgttaccat caccaacaat cgtctgaata actccaaaat | 520 |
| ctacatcaac ggccgtctga tcgaccagaa accgatctcc | 560 |
| aatctgggta acatccacgc ttctaataac atcatgttca | 600 |
| aactggacgg ttgtcgtgac actcaccgct acatctggat | 640 |
| caaatacttc aatctgttcg acaaagaact gaacgaaaaa | 680 |
| gaaatcaaag acctgtacga caaccagtcc aattctggta | 720 |
| tcctgaaaga cttctggggt gactacctgc agtacgacaa | 760 |
| accgtactac atgctgaatc tgtacgatcc gaacaaatac | 800 |
| gttgacgtca acaatgtagg tatccgcggt tacatgtacc | 840 |
| tgaaaggtcc gcgtggttct gttatgacta ccaacatcta | 880 |
| cctgaactct tccctgtacc gtggtaccaa attcatcatc | 920 |
| aagaaatacg cgtctggtaa caaggacaat atcgttcgca | 960 |
| acaatgatcg tgtatacatc aatgttgtag ttaagaacaa | 1000 |
| agaataccgt ctggctacca atgcttctca ggctggtgta | 1040 |
| gaaaagatct tgtctgctct ggaaatcccg gacgttggta | 1080 |
| atctgtctca ggtagttgta atgaaatcca agaacgacca | 1120 |
| gggtatcact aacaaatgca aaatgaatct gcaggacaac | 1160 |
| aatggtaacg atatcggttt catcggtttc caccagttca | 1200 |
| acaatatcgc taaactggtt gcttccaact ggtacaatcg | 1240 |
| tcagatcgaa cgttcctctc gcactctggg ttgctcttgg | 1280 |
| gagttcatcc cggttgatga cggttggggt gaacgtccgc | 1320 |
| tgtaacccgg gaaagctt | 1338 |

<210> SEQ ID NO 2
<211> LENGTH: 1341
<212> TYPE: DNA
<213> ORGANISM: Artificial
<220> FEATURE:
<223> OTHER INFORMATION: /note="synthetic sequence encoding botulinum neurotoxin"

<400> SEQUENCE: 2

| | |
|---|---|
| gaattcacga tggccaacaa atacaattcc gaaatcctga | 40 |
| acaatatcat cctgaacctg cgttacaaag acaacaatct | 80 |
| gatcgatctg tctggttacg gtgctaaagt tgaagtatac | 120 |
| gacgctgttg aactgaatga caagaaccag ttcaaactga | 160 |
| cctcttccgc taactctaag atccgtgtta ctcagaatca | 200 |
| gaacatcatc ttcaactccg tattcctgga cttctctgtt | 240 |
| tccttctgga ttcgtatccc gaaatacaag aacgacggta | 280 |
| tccagaatta catcccacaa tgaatacacca tcatcaactg | 320 |
| catgaagaat aactctggtt ggaagatctc catccgcggt | 360 |

```
aaccgtatca tctggactct gatcgatatc aacggtaaga                400
ccaaatctgt attcttcgaa tacaacatcc gtgaagacat                440
ctctgaatac atcaatcgct ggttcttcgt taccatcacc                480
aataacctga acaatgctaa atctacatc aacggtaaac                 520 tggaatctaa taccgacatc aaagacatcc gtgaagttat                560
cgctaacggt gaaatcatct tcaaactgga cggtgacatc                600
gatcgtaccc agttcatctg gatgaaatac ttctccatct                640
tcaacaccga actgtctcag tccaatatcg aagaacggta                680
caagatccag tcttactccg aatacctgaa agacttctgg                720
ggtaatccgc tgatgtacaa caaagaatac tatatgttca                760
atgctggtaa caagaactct tacatcaaac tgaagaaaga                800
ctctccggtt ggtgaaatcc tgactcgttc caaatacaac                840
cagaactcta aatacatcaa ctaccgcgac ctgtacatcg                880
gtgaaaagtt catcatccgt cgcaaatcta actctcagtc                920
catcaatgat gacatcgtac gtaaagaaga ctacatctac                960
ctggacttct tcaacctgaa tcaggaatgg cgtgtataca                1000
cctacaagta cttcaagaaa gaagaagaaa agcttttcct                1040
ggctccgatc tctgattccg acgaactcta caacaccatc                1080
cagatcaaag aatacgacga acagccgacc tactcttgcc                1120
agctgctgtt caagaaagat gaagaatcta ctgacgaaat                1160
cggtctgatc ggtatccacc gtttctacga atctggtatc                1200
gtattcgaag aatacaaaga ctacttctgc atctccaaat                1240
ggtacctgaa ggaagttaaa cgcaaaccgt acaacctgaa                1280
actgggttgc aattggcagt tcatcccgaa agacgaaggt                1320
tggaccgaat agtaagaatt c                                    1341
```

<210> SEQ ID NO 3
<211> LENGTH: 1371
<212> TYPE: DNA
<213> ORGANISM: Artificial
<220> FEATURE:
<223> OTHER INFORMATION: /note="synthetic sequence encoding botulinum neurotoxin"

<400> SEQUENCE: 3

```
gaattcacga tcaccatccc attcaacatc ttctcctaca                40
ccaacaactc cctgttgaag acatcatca acgagtactt                 80 caacaacatc aacgactcca agatcctgtc cctgcagaac                120
cgtaagaaca ccttggtcga cacctccggt tacaacgccg                160
aggtctccga ggagggtgac gtccagctga acccaatctt                200
cccattcgac ttcaagctgg gttcctccgg tgaggacaga                240
ggtaaggtca tcgtcaccca gaacgagaac atcgtctaca                280
actccatgta cgagtccttc tccatctcct tctggatcag                320
aatcaacaag tgggtctcca acttgccagg ttacaccatc                360
```

-continued

| | |
|---|---|
| atcgactccg tcaagaacaa ctccggttgg tccatcggta | 400 |
| tcatctccac cttcctggtc ttcaccctga agcagaacga | 440 |
| ggactccgag cagtccatca acttctccta cgacatctcc | 480 |
| aacaacgctc ctggttacaa caagtggttc ttcgtcaccg | 520 |
| tcaccaacaa catgatgggt aacatgaaga tctacatcaa | 560 |
| cggtaagctg atcgacacca tcaaggtcaa ggagttgacc | 600 |
| ggtatcaact tctccaagac catcaccttc gagatcaaca | 640 |
| agatcccaga caccggtctg atcacctccg actccgacaa | 680 |
| tatcaacatg tggatccgtg acttctacat cttcgccaag | 720 |
| gagttggacg gtaaggacat caacatcctg ttcaactcct | 760 |
| tgcagtacac caacgtcgtc aaggactact ggggtaacga | 800 |
| cctgagatac aacaaggagt actacatggt caacatcgac | 840 |
| tacttgaaca gatacatgta cgccaactcc agacagatcg | 880 |
| tcttcaacac cagacgtaac aacaacgact caacgagggg | 920 |
| ttacaagatc atcatcaagc gtatcagagg taacaccaac | 960 |
| gacaccagag tcagaggtgg tgacatcctg tacttcgaca | 1000 |
| tgactatcaa caacaaggcc tacaacctgt tcatgaagaa | 1040 |
| cgagaccatg tacgccgaca accactccac cgaggacatc | 1080 |
| tacgccatcg gtctgcgtga gcagaccaag gacatcaacg | 1120 |
| acaacatcat cttccagatc cagccaatga acaaacactta | 1160 |
| ctactacgct tcccagatct tcaagtccaa cttcaacggt | 1200 |
| gagaacatct ccggtatctg ttccatcggt acctacagat | 1240 |
| tccgtctggg tggtgactgg tacagacaca actacttggt | 1280 |
| tccaactgtc aagcagggta actacgcctc cttgctggag | 1320 |
| tccacttcca cccactgggg attcgtccca gtctccgagt | 1360 |
| aataggaatt c | 1371 |

<210> SEQ ID NO 4
<211> LENGTH: 1400
<212> TYPE: DNA
<213> ORGANISM: Artificial
<220> FEATURE:
<223> OTHER INFORMATION: /note="synthetic sequence encoding botulinum neurotoxin"

<400> SEQUENCE: 4

| | |
|---|---|
| gaattcacca tgggagagag tcagcaagaa ctaaattcta | 40 |
| tggtaactga taccctaaat aatagtattc cttttaagct | 80 |
| ttcttcttat acagatgata aattttaat ttcctacttc | 120 |
| aacaagttct tcaagagaat taagtcttct tccgttttaa | 160 |
| acatgagata caagaatgat aaatacgtcg acacttccgg | 200 |
| ttacgactcc aatatcaaca ttaacggtga cgtgtacaag | 240 |
| tacccaacta caaaaaacca attcggtatc tacaacgaca | 280 |
| agcttactga gctgaacatc tctcaaaacg actacattat | 320 |

-continued

| | |
|---|---|
| ctacgacaac aagtacaaga acttctctat ttctttctgg | 360 |
| gtcaggattc ctaactacga caacaagatc gtcaacgtta | 400 |
| acaacgagta cactatcatc aactgtatga gagacaacaa | 440 |
| ctccggttgg aaggtctctc ttaaccacaa cgagatcatt | 480 |
| tggaccttgc aagacaacgc aggtattaac caaaagttag | 520 |
| cattcaacta cggtaacgca acggtatttt ctgactacat | 560 |
| caacaagtgg attttcgtca ctatcactaa cgacagatta | 600 |
| ggtgactcta agctttacat taacggtaac ttaatcgacc | 640 |
| aaaagtccat tttaaactta ggtaacattc acgtttctga | 680 |
| caacatctta ttcaagatcg ttaactgcag ttacaccaga | 720 |
| tacattggca ttagatactt caacattttc gacaaggagt | 760 |
| tagacgagac cgagattcaa actttataca gcaacgaacc | 800 |
| taacaccaat attttgaagg acttctgggg taactacttg | 840 |
| ctttacgaca aggaatacta cttattaaac gtgttaaagc | 880 |
| caaacaactt cattgatagg agaaaggatt ctactttaag | 920 |
| cattaacaac atcagaagca ctattctttt agctaacaga | 960 |
| ttatactctg gtatcaaggt taagatccaa agagttaaca | 1000 |
| actcttctac taacgataac cttgttagaa agaacgatca | 1040 |
| ggtctatatt aacttcgtcg ctagcaagac tcacttattc | 1080 |
| ccattatatg ctgataccgc taccaccaac aaggagaaga | 1120 |
| ccatcaagat ctcctcctct ggcaacagat ttaaccaatg | 1160 |
| cgtcgttatg aactccgtcg gtaacaactg taccatgaac | 1200 |
| tttaaaaata ataatggaaa taatattggg ttgttaggtt | 1240 |
| tcaaggcaga tactgtagtt gctagtactt ggtattatac | 1280 |
| ccacatgaga gatcacacca acagcaatgg atgtttttgg | 1320 |
| aactttattt ctgaagaaca tggatggcaa gaaaaataat | 1360 |
| agggatccgc ggccgcacgc gtcccgggac tagtgaattc | 1400 |

<210> SEQ ID NO 5
<211> LENGTH: 1317
<212> TYPE: DNA
<213> ORGANISM: Artificial
<220> FEATURE:
<223> OTHER INFORMATION: /note="synthetic sequence encoding botulinum neurotoxin"

<400> SEQUENCE: 5

| | |
|---|---|
| gaattcacga tgtcctacac caacgacaag atcctgatct | 40 |
| tgtacttcaa caagctgtac aagaagatca aggacaactc | 80 |
| catcttggac atgagatacg aaaacaataa gttcatcgac | 120 |
| atctccggtt acggttccaa catctccatc aacggtgacg | 160 |
| tctacatcta ctccaccaat agaaaccagt tcggaatcta | 200 |
| ctcctccaag ccttccgagg tcaacatcgc tcagaacaac | 240 |
| gacatcatct acaacggaag ataccagaac ttctccatgt | 280 |

-continued

| | |
|---|---|
| ccttctgggt ccgtatccca aagtacttca acaaggtcaa | 320 |
| cctgaataac gagtacacca tcatcgactg catccgtaac | 360 |
| aataactccg gatggaagat ctccctgaac tacaacaaga | 400 |
| tcatctggac cctgcaggac accgccggta acaatcagaa | 440 |
| gttggtcttc aactacaccc agatgatctc catctccgac | 480 |
| tacatcaaca gtggatcttc cgtcaccatc accaataacc | 520 |
| gtttgggaaa ctccagaatc tacatcaacg gtaacttgat | 560 |
| cgacgagaag tccatctcca acttgggtga catccacgtc | 600 |
| tccgacaaca ttttgttcaa gatcgtcggt tgtaacgaca | 640 |
| cccgttacgt cgggatccgt tacttcaaag tcttcgacac | 680 |
| tgagttgggt aagaccgaga tcgagaccct gtactcccac | 720 |
| gagcctgacc catccatcct gaaggacttc tggggtaact | 760 |
| acctgctgta caacaaacgt tactacttgc tgaacctgtt | 800 |
| gcgtaccgac aagtccatca cccagaactc caacttcttg | 840 |
| aacatcaacc agcagagagg tgtctaccag aagccaaaca | 880 |
| tcttctccaa caccagattg tacaccggag tcgagttcat | 920 |
| tatcagaaag aacggatcta ctgatatttc caacaccgat | 960 |
| aacttcgtca gaaagaacga tctggcttac atcaacgttc | 1000 |
| tcgacagaga tgtcgaatac cgtctgaacg ccgatatctc | 1040 |
| tatcgccaaa cctgaaaaga tcatcaagct gatccgtacc | 1080 |
| tctaactcta caactctct gggacaaatc atcgtcatgg | 1120 |
| actccatcgg taataactgt accatgaact tccagaacaa | 1160 |
| caacggtgga acatcggtt tgttgggttt ccactccaac | 1200 |
| aacttggtcg cttcctcctg gtactacaac aacatccgta | 1240 |
| agaacacctc ctccaacggt tgcttctggt ccttcatctc | 1280 |
| caaggagcac ggttggcagg agaactaata ggaattc | 1317 |

<210> SEQ ID NO 6
<211> LENGTH: 1347
<212> TYPE: DNA
<213> ORGANISM: Artificial
<220> FEATURE:
<223> OTHER INFORMATION: /note="synthetic sequence encoding botulinum neurotoxin"

<400> SEQUENCE: 6

| | |
|---|---|
| atgaaggaca ccatcctgat ccaggtcttc aacaactaca | 40 |
| tctccaacat ctcctccaac gccatcctgt ccctgtccta | 80 |
| ccgtggtggt cgtctgatcg actcctccgg ttacggagcc | 120 |
| accatcaacg tcggttccga cgtcatcttc aacgacatcg | 160 |
| gtaacggtca gttcaagctg aacaactccg agaactccaa | 200 |
| catcaccgcc accagtcca gttcgtcgt ctacgactcc | 240 |
| atgttcgaca cttctccat caacttctgg gtccgtaccc | 280 |
| caaagtacaa caacaacgac atccagacct acctgcagaa | 320 |

-continued

| | |
|---|---|
| cgagtacacc atcatctcct gtatcaagaa cgactccggt | 360 |
| tggaaggtct ccatcaaggg aaaccgtatc atctggaccc | 400 |
| tgatcgacgt caacgccaag tccaagtcca tcttcttcga | 440 |
| gtactccatc aaggacaaca tctccgacta catcaacaag | 480 |
| tggttctcca tcaccatcac caacgaccgt ctgggtaacg | 520 |
| ccaacatcta catcaacggt tccctgaaga agtccgagaa | 560 |
| gatcctgaac ctggaccgta tcaactcctc caacgacatc | 600 |
| gacttcaagc tgatgaactg taccgacacc accaagttcg | 640 |
| tctggatcaa ggacttcaac atcttcggtc gtgagctgaa | 680 |
| cgccaccgag gtctcctccc tgtactggat ccagtcctcc | 720 |
| accaacaccc tgaaggactt ctggggaaac ccactgcgtt | 760 |
| acgacaccca gtactacctg ttcaaccagg gtatgcagaa | 800 |
| catctacatc aagtacttct ccaaggcctc catgggtgag | 840 |
| accgcccctc gtaccaactt caacaacgcc gccatcaact | 880 |
| accagaacct gtacctgggt ctgcgtttca tcatcaagaa | 920 |
| ggcctccaac tcccgtaaca tcaacaacga caacatcgtc | 960 |
| cgtgagggtg actacatcta cctgaacatc gacaacatct | 1000 |
| ccgacgagtc ctaccgtgtc tacgtcctgg tcaactccaa | 1040 |
| ggagatccag acccagctgt tcctggcccc aatcaacgac | 1080 |
| gaccctacct tctacgacgt cctgcagatc aagaagtact | 1120 |
| acgagaagac cacctacaac tgtcagatcc tgtgcgagaa | 1160 |
| ggacaccaag accttcggac tgttcggtat cggtaagttc | 1200 |
| gtcaaggact acggttacgt ctgggacacc tacgacaact | 1240 |
| acttctgtat ctcccagtgg tacctgcgtc gtatctccga | 1280 |
| gaacatcaac aagctgcgtc tgggatgtaa ctggcagttc | 1320 |
| atcccagtcg acgagggttg gaccgag | 1347 |

<210> SEQ ID NO 7
<211> LENGTH: 2452
<212> TYPE: DNA
<213> ORGANISM: Clostridium botulinum
<220> FEATURE:

<400> SEQUENCE: 7

| | |
|---|---|
| atgatcaaag ttaataattg ggacttgttt tttagtcctt | 40 |
| cagaagataa ttttactaat gatctaaata aaggagaaga | 80 |
| aattacatct gatactaata tagaagcagc agaagaaaat | 120 |
| attagtttag atttaataca acaatattat ttaacctta | 160 |
| attttgataa tgaacctgaa atatttcaa tagaaaatct | 200 |
| ttcaagtgac attataggcc aattagaact tatgcctaat | 240 |
| atagaaagat ttcctaatgg aaaaaagtat gagttagata | 280 |
| aatatactat gttccattat cttcgtgctc aagaatttga | 320 |
| acatggtaaa tctaggattg ctttaacaaa ttctgttaac | 360 |

-continued

```
gaagcattat taaatcctag tcgtgtttat acattttttt         400
cttcagacta tgtaaagaaa gttaataaag ctacggaggc         440
agctatgttt ttaggctggg tagaacaatt agtatatgat         480
tttaccgatg aaactagcga agtaagtact acggataaaa         520
ttgcggatat aactataatt attcctttaa tattttcagg         560
agctgttatt ctgttagaat ttataccaga gattgcaata         600
cctgtattag gtacttttgc acttgtatca tatattgcga         640
ataaggttct aaccgttcaa acaatagata atgctttaag         680
taaaagaaat gaaaaatggg atgaggtcta aaatatata          720 gtaacaaatt ggttagcaaa ggttaataca cagattgatc         760
taataagaaa aaaaatgaaa gaagctttag aaaatcaagc         800
agaagcaaca aaggctataa taaactatca gtataatcaa         840
tatactgagg aagagaaaaa taatattaat tttaatattg         880
atgatttaag ttcgaaactt aatgagtcta taaataaagc         920
tatgattaat ataaataaat ttttgaatca atgctctgtt         960
tcatatttaa tgaattctat gatcccttat ggtgttaaac        1000
ggttagaaga ttttgatgct agtcttaaag atgcattatt        1040
aaagtatata tatgaacttt aattggtcaa gtagatagat        1080
taaaagataa agttaataat acacttagta cagatatacc        1120
ttttcagctt tccaaatacg tagataatca aagattatta        1160
tctacattta ctgaatatat taagaatatt attaatactt        1200
ctatattgaa tttaagatat gaaagtaatc atttaataga        1240
cttatctagg tatgcatcaa aaataaatat tggtagtaaa        1280
gtaaattttg atccaataga taaaaatcaa attcaattat        1320
ttaatttaga aagtagtaaa attgaggtaa ttttaaaaaa        1360
tgctattgta tataatagta tgtatgaaaa ttttagtact        1400
agcttttgga taagaattcc taagtatttt aacagtataa        1440
gtctaaataa tgaatataca ataataaatt gtatggaaaa        1480
taattcagga tggaaagtat cacttaatta tggtgaaata        1520
atctggactt tacaggatac tcaggaaata aaacaaagag        1560
tagtttttaa atacagtcaa atgattaata tatcaacaga        1600
tggatttttg taactatcac taataataga ttaaataact        1640
ctaaaattta tataaatgga agattaatag atcaaaaacc        1680
aatttcaaat ttaggtaata ttcatgctag taataatata        1720
atgtttaaat tagatggttg tagagataca catagatata        1760
tttggataaa atattttaat cttttttgata aggaattaaa        1800 tgaaaagaa atcaaagatt tatatgataa tcaatcaaat         1840
tcaggtattt taaagacttt tgggggtgat tatttacaat        1880
atgataaacc atactatatg ttaaatttat atgatccaaa        1920
taaatatgtc gatgtaaata atgtaggtat tagaggttat        1960
```

| | |
|---|---|
| atgtatctta aagggcctag aggtagcgta atgactacaa | 2000 |
| acatttattt aaattcaagt ttgtataggg ggacaaaatt | 2040 |
| tattataaaa aaatatgctt ctggaaataa agataatatt | 2080 |
| gttagaaata atgatcgtgt atatattaat gtagtagtta | 2120 |
| aaaataaaga atataggtta gctactaatg catcacaggc | 2160 |
| aggcgtagaa aaaatactaa gtgcattaga aatacctgat | 2200 |
| gtaggaaatc taagtcaagt agtagtaatg aagtcaaaaa | 2240 |
| atgatcaagg aataacaaat aaatgcaaaa tgaatttaca | 2280 |
| agataataat gggaatgata taggctttat aggatttcat | 2320 |
| cagtttaata atatagctaa actagtagca agtaattggt | 2360 |
| ataatagaca aatagaaaga tctagtagga ctttgggttg | 2400 |
| ctcatgggaa tttattcctg tagatgatgg atggggagaa | 2440 |
| aggccactgt aa | 2452 |

<210> SEQ ID NO 8
<211> LENGTH: 1987
<212> TYPE: DNA
<213> ORGANISM: Clostridium botulinum
<220> FEATURE:

<400> SEQUENCE: 8

| | |
|---|---|
| atgatcaaag ttaataattg ggacttgttt tttagtcctt | 40 |
| cagaagataa ttttactaat gatctaaata aaggagaaga | 80 |
| aattacatct gatactaata tagaagcagc agaagaaaat | 120 |
| attagtttag atttaataca acaatattat ttaaccttta | 160 |
| attttgataa tgaacctgaa atatttcaa tagaaaatct | 200 |
| ttcaagtgac attataggcc aattagaact tatgcctaat | 240 |
| atagaaagat ttcctaatgg aaaaaagtat gagttagata | 280 |
| aatatactat gttccattat cttcgtgctc aagaatttga | 320 |
| acatggtaaa tctaggattg cttttaacaaa ttctgttaac | 360 |
| gaagctgctc aagaatttga acatggtaaa tctaggattg | 400 |
| ctttaacaaa ttctgttaac gaagcattat taaatcctag | 440 |
| tcgtgtttat acatttttt cttcagacta tgtaaagaaa | 480 |
| gttaataaag ctacggaggc agctatgttt ttaggctggg | 520 |
| tagaacaatt agtatatgat tttaccgatg aaactagcga | 560 |
| agtaagtact acggataaaa ttgcggatat aactataatt | 600 |
| attccatata taggacctgc tttaaatata ggtaatatgt | 640 |
| tatataaaga tgattttgta ggtgctttaa tattttcagg | 680 |
| agctgttatt ctgttagaat ttataccaga gattgcaata | 720 |
| cctgtattag gtacttttgc acttgtatca tatattgcga | 760 |
| ataaggttct aaccgttcaa acaatagata atgctttaag | 800 |
| taaaagaaat gaaaaatggg atgaggtcta taaatatata | 840 |
| gtaacaaatt ggttagcaaa ggttaataca cagattgatc | 880 |

-continued

| | |
|---|---|
| taataagaaa aaaaatgaaa gaagctttag aaaatcaagc | 920 |
| agaagcaaca aaggctataa taaactatca gtataatcaa | 960 |
| tatactgagg aagagaaaaa taatattaat tttaatattg | 1000 |
| atgatttaag ttcgaaactt aatgagtcta taaataaagc | 1040 |
| tatgattaat ataaataaat ttttgaatca atgctctgtt | 1080 |
| tcatatttaa tgaattctat gatcccttat ggtgttaaac | 1120 |
| ggttagaaga ttttgatgct agtcttaaag atgcattatt | 1160 |
| aaagtatata tatgataata gaggaactttt aattggtcaa | 1200 |
| gtagatagat taaaagataa agttaataat acacttagta | 1240 |
| cagatatacc ttttcagctt tccaaatacg tagataatca | 1280 |
| aagattatta tctacattta ctgaatatat taagaatatt | 1320 |
| attaatactt ctatattgaa tttaagatat gaaagtaatc | 1360 |
| atttaataga cttatctagg tatgcatcaa aaataaatat | 1400 |
| tggtagtaaa gtaaattttg atccaataga taaaaatcaa | 1440 |
| attcaattat ttaatttaga aagtagtaaa attgaggtaa | 1480 |
| ttttaaaaaa tgctattgta tataatagta tgtatgaaaa | 1520 |
| ttttagtact agcttttgga taagaattcc taagtatttt | 1560 |
| aacagtataa gtctaaataa tgaatataca ataataaatt | 1600 |
| gtatggaaaa taattcagga tggaaagtat cacttaatta | 1640 |
| tggtgaaata atctggactt tacaggatac tcaggaaata | 1680 |
| aaacaaagag tagtttttaa atacagtcaa atgattaata | 1720 |
| tatcagatta tataaacaga tggattttg taactatcac | 1760 |
| taataataga ttaaataact ctaaataact ctaaaattta | 1800 |
| tataaatgga agattaatag atcaaaaacc aatttcaaat | 1840 |
| ttaggtaata ttcatgctag taataatata atgtttaaat | 1880 |
| tagatggttg tagagataca catagatata tttggataaa | 1920 |
| atattttaat cttttgata aggaattaaa tgaaaagaa | 1960 |
| atcaaagatt tatatgataa tcaataa | 1987 |

<210> SEQ ID NO 9
<211> LENGTH: 1327
<212> TYPE: DNA
<213> ORGANISM: Clostridium botulinum
<220> FEATURE:

<400> SEQUENCE: 9

| | |
|---|---|
| atgcaaagat tattatctac atttactgaa tatattaaga | 40 |
| atattattaa tacttctata ttgaatttaa gatatgaaag | 80 |
| taatcattta atagacttat ctaggtatgc atcaaaaata | 120 |
| aatattggta gtaaagtaaa ttttgatcca atagataaaa | 160 |
| atcaaattca attatttaat ttagaaagta gtaaaattga | 200 |
| ggtaatttta aaaaatgcta ttgtatataa tagtatgtat | 240 |
| gaaaattttta gtactagctt ttggataaga attcctaagt | 280 |

```
atttttaacag tataagtcta aataatgaat atacaataat            320
aaattgtatg gaaaataatt caggatggaa agtatcactt            360
aattatggtg aaataatctg gactttacag gatactcagg            400
aaataaaaca aagagtagtt tttaaataca gtcaaatgat            440
taatatatca gattatataa acagatggat ttttgtaact            480
atcactaata atagattaaa taactctaaa atttatataa            520
atggaagatt aatagatcaa aaaccaattt caaatttagg            560
taatattcat gctagtaata atataatgtt taaattagat            600
ggttgtagag atacacatag atatatttgg ataaaatatt            640
ttaatctttt tgataaggaa ttaaatgaaa aagaaatcaa            680
agatttatat gataatcaat caaattcagg tatttttaaaa           720 gacttttggg gtgattattt acaatatgat aaaccatact            760
atatgttaaa tttatatgat ccaaataaat atgtcgatgt            800
aaataatgta ggtattagag gttatatgta tcttaaaggg            840
cctagaggta gcgtaatgac tacaaatgac tacaaacatt            880
tatttaaatt caagtttgta taggggggaca aaatttatta           920 taaaaaaata tgcttctgga aataaagata atattgttag            960
aaataatgat cgtgtatata ttaatgtagt agttaaaaat           1000
aaagaatata ggttagctac taatgcatca caggcaggcg           1040
tagaaaaaat actaagtgca ttagaaatac ctgatgtagg           1080
aaatctaagt caagtagtag taatgaagtc aaaaaatgat           1120
caaggaataa caaataaatg caaatgaat ttacaagata            1160 ataatgggaa tgatataggc tttataggat ttcatcagtt           1200
taataatata gctaaactag tagcaagtaa ttggtataat           1240
agacaaatag aaagatctag taggactttg ggttgctcat           1280
gggaatttat tcctgtagat gatggatggg gagaaaggcc           1320
actgtaa                                              1327

<210> SEQ ID NO 10
<211> LENGTH: 702
<212> TYPE: DNA
<213> ORGANISM: Clostridium botulinum
<220> FEATURE:

<400> SEQUENCE: 10
atggctcgtc tgctgtctac cttcactgaa tacatcaaga             40
acatcatcaa tacctccatc ctgaacctgc gctacgaatc             80
caatcacctg atcgacctgt ctcgctacgc ttccaaaatc            120
aacatcggtt ctaaagttaa cttcgatccg atcgacaaga            160
atcagatcca gctgttcaat ctggaatctt ccaaaatcga            200
agttatcctg aagaatgcta tcgtatacaa ctctatgtac            240
gaaaacttct ccacctcctt ctggatccgt atcccgaaat            280
acttcaactc catctctctg aacaatgaat acaccatcat            320
```

-continued

```
caactgcatg gaaaacaatt ctggttggaa agtatctctg          360
aactacggtg aaatcatctg gactctgcag gacactcagg          400
aaatcaaaca gcgtgttgta ttcaaatact ctcagatgat          440
caacatctct gactacatca atcgctggat cttcgttacc          480
atcaccaaca atcgtctgaa taactccaaa atctacatca          520
acggccgtct gatcgaccag aaaccgatct ccaatctggg          560
taacatccac gcttctaata acatcatgtt caaactggac          600
ggttgtcgtg acactcaccg ctacatctgg atcaaatact          640
tcaatctgtt cgacaaagaa ctgaacgaaa agaaatcaa           680 agacctgtac gacaaccagt aa                            702

<210> SEQ ID NO 11
<211> LENGTH: 621
<212> TYPE: DNA
<213> ORGANISM: Clostridium botulinum
<220> FEATURE:

<400> SEQUENCE: 11
atgtccaatt ctggtatcct gaaagacttc tggggtgact          40
acctgcagta cgacaaaccg tactacatgc tgaatctgta          80
cgatccgaac aaatacgttg acgtcaacaa tgtaggtatc         120
cgcggttaca tgtacctgaa aggtccgcgt ggttctgtta         160
tgactaccaa catctacctg aactcttccc tgtaccgtgg         200
taccaaattc atcatcaaga aatacgcgtc tggtaacaag         240
gacaatatcg ttcgcaacaa tgatcgtgta tacatcaatg         280
ttgtagttaa gaacaaagaa taccgtctgg ctaccaatgc         320
ttctcaggct ggtgtagaaa agatcttgtc tgctctggaa         360
atcccggacg ttggtaatct gtctcaggta gttgtaatga         400
aatccaagaa cgaccagggt atcactaaca aatgcaaaat         440
gaatctgcag gacaacaatg gtaacgatat cggtttcatc         480
ggtttccacc agttcaacaa tatcgctaaa ctggttgctt         520
ccaactggta caatcgtcag atcgaacgtt cctctcgcac         560
tctgggttgc tcttgggagt tcatcccggt tgatgacggt         600
tggggtgaac gtccgctgta a                            621
```

BOTULINUM NEUROTOXIN VACCINE

This application is a continuation-in-part of U.S. application Ser. No. 08/981,159, filed Nov. 10, 1997, which is a national stage application of PCT/US96/07454, filed May 21, 1996, which is a continuation-in-part of U.S. application Ser. No. 09/448,630, filed May 23, 1995, now U.S. Pat. No. 5,792,462. This application also claims the benefit of provisional applications 60/092,416, filed Jul. 10, 1998, and 60/133,870, filed May 12, 1999.

FIELD OF THE INVENTION

This invention relates to vaccines for bacterial toxins from *Clostridium botulinum*.

INTRODUCTION

Botulism is a disease resulting from the activity of botulinum neurotoxin produced by *Clostridium botulinum* on the transmission of neuromuscular stimuli. The blockage of stimuli produces neuromuscular weakness and flaccid paralysis which can lead to respiratory failure and death. Food poisoning, infant botulism, and wound botulism are the three ways in which humans are naturally affected by botulinum neurotoxin (BoNT). Ingestion of improperly prepared or canned foods has resulted in numerous cases of botulism. Seven different serotypes of botulinum neurotoxin have been characterized, types A through G, which are antigenically distinct. BoNT are usually expressed in *Clostridium botulinum* as a single polypeptide chain and then posttranslationally nicked, forming a dichain consisting of a 100-kDa heavy chain and a 50-kDa light chain held together by a single disulfide bond (DasGupta, B. R. 1989, In L. L. simpson (ed.), *Botulinum Neurotoxin and Tetanus Toxin*. Academic Press, New York, N.Y.). Topologically, these neurotoxins are composed of three domains, a binding domain, a translocation domain, and a catalytic domain, each of which is believed to play a role in intoxication. The carboxy-terminal portion of the heavy chain is responsible for binding nerve cell receptor(s). After toxin binding, it is thought to be internalized into an endosome through receptor-mediated endocytosis (Byrne, M. P. et al., 1998, supra). The product of a gene encoding only the binding domain of BoNT is nontoxic when administered to an organism since it cannot enter the nerve cell without the translocation domain and it lacks the catalytic domain.

The vaccine currently used against botulism is comprised of the complete toxoid (Byrne, M. P. et al., *Infect. Immun.* 66:4817, 1998). The toxoid vaccine is dangerous and expensive to produce, contains formalin, which is very painful for the recipient, and is incomplete; only five, A–E, of the seven serotypes are represented in the formulation.

Previous work with BoNT serotype A (BoNT/A) demonstrated that the recombinant carboxy terminal of the heavy chain polypeptide (Hc fragment) produced in *Escherichia coli* only partially protected mice challenged with up to 1,200 $LD_{50}$ of BoNT/A (LaPenotiere, H. F. et al., 1995, *Toxicon* 33:1383-1386; Clayton, M. A. et al., 1995, *Infect. Immun.* 63: 2738–2742). This preparation was difficult to produce due to inclusion bodies and the resulting amount of polypeptide was not large enough to justify large scale production. Furthermore, the product contained *E. coli* endotoxin.

Therefore, there is a need for an efficacious vaccine against botulism, useful for protecting humans.

SUMMARY OF THE INVENTION

The present invention satisfies the need discussed above. The present invention relates to a method and composition for use in inducing an immune response which is protective against intoxication with botulinum neurtoxin (BoNT) serotypes A (BoNTA), B (BoNTB), C (BoNTC), D (BoNTD), E (BoNTE), and F (BoNTF), and G (BoNTG). The invention relates to the use of a replicon vector which results in production of large amounts of a protein encoded by a sequence cloned into the replicon. The protein product is easily purified, available in large quantities, and devoid of endotoxin. Furthermore, immunization with the replicon encoding the desired antigen has the advantage of expressing genes in lymph nodes for a better immune response, and for stimulating mucosal immune responses (Davis et al., 1996, *J. Virol.* 70, 3781–3787).

The sequences encoding the Hc 50,000 Kd nontoxic fragment of BoNT A–G (see attached sequence and Clayton et al., 1995, *Infection and Immunity* 63, 2738 –2742) were inserted into the Venezuelan equine encephalitis (VEE) virus replicon described in U.S. Pat. No. 5,792,462 (Hc-replicon). In this vaccine strategy, a gene coding for a protein of interest is cloned in place of the VEE virus structural genes; the result is a self-replicating RNA molecule that encodes its own replicase and transcriptase functions, and in addition makes abundant quantities of mRNA encoding the foreign protein. When replicon RNA is transfected into eukaryotic cells along with two helper RNAs that express the VEE structural proteins (glycoproteins and nucleocapsid), the replicon RNA is packaged into VEE virus-like particles by the VEE virus structural proteins, which are provided in trans. Since the helper RNAs lack packaging signals neccessary for further propagation, the resulting VEE replicon particles (VRPs) which are produced are infectious for one cycle but are defective thereafter. Upon infection of an individual cell with a VRP, an abortive infection occurs in which the infected cell produces the protein of interest in abundance, is ultimately killed by the infection, but does not produce any viral progeny (Pushko et al., 1997, *Virology* 239, 389–401).

Experiments carried out in cell culture using the Hc-replicon demonstrated that the construct could produce high levels of the Hc polypeptides in eukaryotic cells. Inoculation of VRP containing the Hc-replicon into an inbred mouse strain (BALB/c) or into an outbred mouse strain (SWISS) produced high antibody titers and protected the mice from the effects of botulinum neurotoxin.

Therefore, it is one object of the present invention to provide a VEE virus replicon vector comprising a VEE virus replicon and a DNA fragment encoding any of the botulinum neurotoxin heavy chain fragments of serotypes A, B, C, D, E, F, G, alone or in combination, and fragments thereof such as ASubHc1 or ASubHc2, which define domains within serotype A toxin.

It is another object of the present invention to provide a self replicating RNA comprising the VEE virus replicon and any of the botulinum neurotoxin fragments described above.

It is another object of the present invention to provide infectious VEE virus replicon particles produced from the VEE virus replicon RNA described above.

It is further an object of the invention to provide an immunological composition for the protection of mammals against botulinum intoxication comprising VEE virus replicon particles containing any of the botulinum neurotoxin fragments described above or a combination of different VEE virus replicons each containing a different botulinum neurotoxin fragment.

BRIEF DESCRIPTION OF THE DRAWINGS

These and other features, aspects, and advantages of the present invention will become better understood with reference to the following description and appended claims, and accompanying drawings where:

FIG. 1. Western blot of BHK cell lysates showing expression of Hc from recombinant VEE replicons. a) infected cell lysate; b) commercially available product.

DETAILED DESCRIPTION

Figure 2:
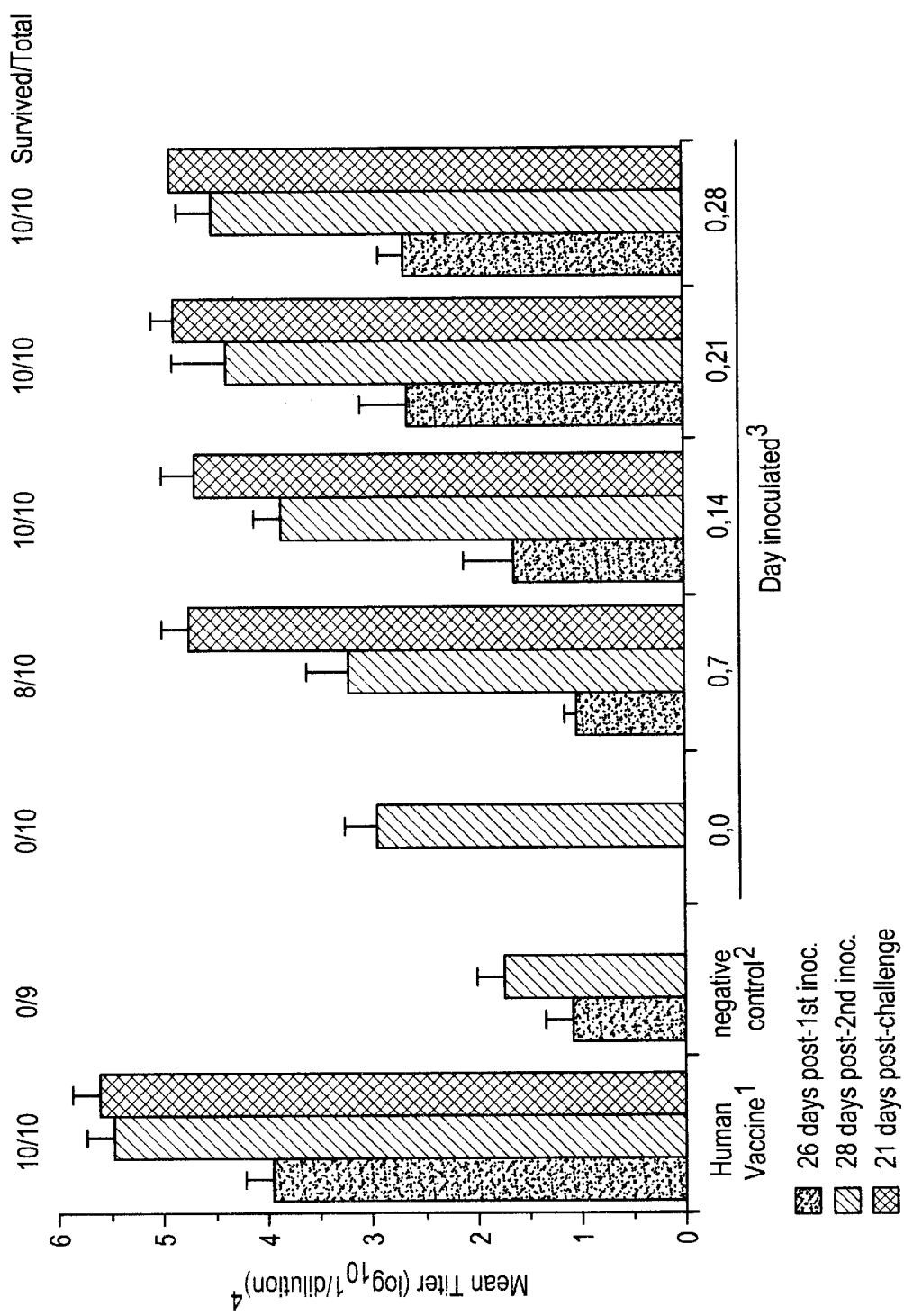
FIG. 2. ELISA titers for Balb/c mice immunized with Hc-VRP at different intervals. 1) 0.2 ml human vaccine given at day 0 and 28; 2) $10^7$ iu Lassa N-VRP given at day 0 and 28; 3) $10^7$ iu Hc-VRP per inoculation; 4) Titers less than 2 logs or greater than 5.61 logs were estimated. Challenge was 31 days after last inoculation with 1000 $LD_{50}$ BoNT/A.

In the description that follows, a number of terms used in recombinant DNA, virology and immunology are extensively utilized. In order to provide a clearer and consistent understanding of the specification and claims, including the scope to be given such terms, the following definitions are provided.

Replicon

A replicon is equivalent to a full length virus from which all of the viral structural proteins have been deleted. A multiple cloning site can be cloned into the site previously occupied by the structural protein genes. Virtually any heterologous gene may be cloned into this cloning site. Transcription of the RNA from the replicon yields an RNA capable of initiating infection of the cell identically to that seen with the full-length infectious virus clone. However, in lieu of the viral structural proteins, the heterologous antigen is expressed. This system does not yield any progeny virus particles because there are no viral structural proteins available to package the RNA into particles.

Particles which appear structurally identical to virus particles can be produced by supplying structural proteins for packaging of the replicon RNA in trans. This is typically done with two helpers also called defective helper RNAs. One helper consists of a full length infectious clone from which the nonstructural protein genes and the glycoprotein genes are deleted. The helper retains only the terminal nucleotide sequences, the promoter for subgenomic mRNA transcription and the sequences for the viral nucleocapsid protein. The second helper is identical to the first except that the nucleocapsid gene is deleted and only the glycoprotein genes are retained. The helper RNA's are transcribed in vitro and co-transfected with replicon RNA. Because the replicon RNA retains the sequences for packaging by the nucleocapsid protein, and because the helpers lack these sequences, only the replicon RNA is packaged by the viral structural proteins and released from the cell. The particles can then by inoculated into animals similar to parent virus. The replicon particles will initiate only a single round of replication because the helpers are absent, they produce no progeny virus particles, and express only the viral nostructural proteins and the product of the heterologous gene cloned in place of the structural proteins.

The VEE virus replicon is a genetically reorganized version of the VEE virus genome in which the structural proteins genes are replaced with a gene from an immunogen of interest, in this invention, the BoNT Hc proteins. The result is a self replicating RNA (replicon) that can be packaged into infectious particles using defective helper RNAs that encode the glycoprotein and capsid proteins of the VEE virus.

Subject

Includes both human, animal, e.g., horse, cattle, donkey, monkey, pig, dog, guinea pig, mouse, hamster, avian e.g., chicken, pheasant or turkey, fish and other marine animals, and insects such as mosquito.

In one embodiment, the present invention relates to a recombinant DNA molecule that includes a VEE replicon and a DNA sequence encoding BoNT proteins. Both native and synthetic DNA sequences encoding BoNT heavy chain were used in this invention. The synthetic BoNT(Hc) DNA fragments were optimized for codon usage for expression in yeast. Other modifications in codon usage which result in a different nucleotide sequence but still produce an immunologically identifiable heavy chain fragment can also be used. The synthetic Hc fragments used in the examples below are as follows: Hc BoNTA (SEQ ID NO:1), Hc BoNTB (SEQ ID NO:2), Hc BoNTC (SEQ ID NO:3), Hc BoNTE (SEQ ID NO:4), Hc BoNTF (SEQ ID NO:5), Hc BoNTG (SEQ ID NO:6). Native DNA sequences encoding heavy chain region of the neurotoxins as well as the carboxy or amino terminus of the heavy chain region of the neurotoxin were used. The native sequence of heavy chain serotype A is known (Thompson, D. E. et al., 1990, *Eur. J. Biochem.* 189, 73–81) and is identified in SEQ ID NO: 7. The amino terminal region of the native heavy chain (SEQ ID NO: 8) and the carboxy terminal region of the native heavy chain (SEQ ID NO:9) were cloned into a replicon vector and are exemplified below. DNA or polynucleotide sequences to which the invention also relates include sequences of at least about 6 nucleotides, preferably at least about 8 nucleotides, more preferably at least about 10–12 nucleotides, most preferably at least about 15–20 nucleotides corresponding, i.e., homologous to or complementary to, a region of the Hc BoNT nucleotide sequences. Regions from which typical DNA sequences may be derived include but are not limited to, for example, regions encoding specific epitopes, as well as non-transcribed and/or non-translated regions.

DNA sequences also embodied in the present invention include the BoNT sequence encoding a subfragment of the Hc. The exemplified subfragments were chosen based on domains within the protein itself (Lacy et al, 1998, *Science* 5, 898–902). The subfragments exemplified were chosen from serotype A Hc fragment (Clayton et al., 1995, supra, GenBank accession number is U22962): AsubHc1 includes amino acid #1 Met to amino acid # 233 Arg (SEQ ID NO:10, nucleotides 9–707 of Genbank U22962) of serotype A Hc fragment, and AsubHc2 includes amino acid # 234 Ser to amino acid # 438 Leu (SEQ ID NO:11, nucleotide 708 to 1325 of Genbank U22962) of serotype A Hc fragment. A methionine was added to AsubHc2 in order to initiate proper translation. Other subfragments of any size can be used for different purposes. For example, a subfragment overlapping the AsubHc1 and AsubHc2 would include epitopes previously broken apart in AsubHc1 and AsubHc2. Methods for manipulating nucleic acid sequences are known in the art, please see e.g., Maniatis, Fritsch and Sambrook, *Molecular Cloning: a Laboratory Manual* (1982) or *DNA Cloning*, volumes I and II (D. N. glover ed. 1985) or *Current Protocols in Molecular Biology*, Ausubel, F. M. et al. (Eds.) John Wiley & Sons, Inc., for general cloning methods.

The derived polynucleotide is not necessarily physically derived from the nucleotide sequence shown in SEQ ID NO:1–11, but may be generated in any manner, including for example, chemical synthesis or DNA replication or reverse transcription or transcription, which are based on the information provided by the sequence of bases in the region(s) from which the polynucleotide is derived. In addition, combinations of regions corresponding to that of the designated sequence may be modified in ways known in the art to be consistent with an intended use. The sequences of the present invention can be used in diagnostic assays such as hybridization assays and polymerase chain reaction assays and for the detection of BoNT sequences. Since the nucleic acid sequence is synthetic, i.e. the codon usage was optimized for expression in a yeast system, it could not be used effectively in hybridization assays without correcting the codon usage for a specific purpose.

In another embodiment, the present invention relates to a recombinant DNA molecule that includes a vector and one or more nucleic acid sequences as described above. The vector can take the form of a plasmid, such as pUC19, or any other vector which replicates in any host such as *E. coli*, yeast, insect cells, or mammalian cells. The recombinant DNA molecule can be used to generate more DNA molecules or, when the nucleic acid sequences are inserted into an expression vector, the protein encoded by the nucleic acid sequence can be produced.

When the DNA sequences described above are in a replicon expression system, such as the VEE replicon described above, the proteins can be expressed in vivo. The DNA sequence for any of the BoNT proteins described above can be cloned into the multiple cloning site of a replicon such that transcription of the RNA from the replicon yields an infectious RNA containing the BoNT sequence encoding a protein or proteins of interest. Use of helper RNA containing sequences necessary for encapsulation of the viral transcript will result in the production of viral particles containing replicon RNA which are able to infect a host and initiate a single round of replication resulting in the expression of the BoNT proteins. Such replicon constructs include those presented in Table 1.

TABLE 1

| Replicon Plasmid Name | Serotype | expresses |
|---|---|---|
| p3014-40A | A | full length synthetic C fragment |
| p3014-114a1 | A | N-terminal sub-synthetic C-fragment |
| p3014-102a2 | A | C-terminal sub-synthetic C-fragment |
| p3014-73B | B | full length synthetic C fragment |
| p3014-110C | C | full length synthetic C fragment |
| p3014-75E | E | full length synthetic C fragment |
| p3014-77F | F | full length synthetic C fragment |
| p3014-107G | G | full length synthetic C fragment |

TABLE 1-continued

| Replicon Plasmid Name | Serotype | expresses |
|---|---|---|
| pXrep-BoNTA/H | A | heavy chain native sequence |
| pXrep-BoNTA/$H_N$ | A | amino terminal of native heavy chain sequence |
| pXrep-BoNTA/$H_C$ | A | carboxy teminal of native heavy chain sequence |

The following plasmids were deposited on Feb. 1, 2002 in the American Type Culture Collection (ATCC), located 10801 University Boulevard, Manassas, Virginia 20110-2209:

p3014-40A, assigned ATCC accession number PTA-4031 p3014-55SEB, assigned ATCC accession number PTA-4032 p3014-56SEA, assigned ATCC accession number PTA-4033 p3014-57SEB, assigned ATCC accession number PTA-4034 p3014-73B, assigned ATCC accession number PTA-4035 p3014-75E, assigned ATCC accession number PTA-4036 p3014-77F, assigned ATCC accession number PTA-4037 p3014-102a2, assigned ATCC accession number PTA-4038 p3014-107G, assigned ATCC accession number PTA-4039 p3014-110C, assigned ATCC accession number PTA-4040

P3014-114a1, assigned ATCC accession number PTA-4041 p3014-MAT-PA, assigned ATCC accession number PTA-4042 p3014-PA, assigned ATCC accession number PTA-4043 p3014-PA63, assigned ATCC accession number PTA-4044 p3014-TPA-PA, assigned ATCC accession number PTA-4045.

The sequences encoding the BoNT proteins were cloned into the replicon vector by methods known in the art and described below in Materials and Methods. Schematic diagrams of the resulting constructs are shown in the Figures. The VEE constructs containing BoNT Hc proteins can be used as a DNA vaccine, or for the production of RNA molecules as described below.

In another embodiment, the present invention relates to RNA molecules resulting from transcription of the constructs described above. The RNA molecules can be prepared by transcription using methods known in the art and described in the Examples below. Alternatively, the RNA molecules can be produced by transcription of the constructs in vivo, and isolating the RNA. These and other methods for obtaining RNA transcripts of the constructs are known in the art. Please see Current *Protocols in Molecular Biology*. Frederick M. Ausubel et al. (eds.), John Wiley and Sons, Inc. The RNA molecules can be used, for example, to transfect cells along with RNA from helper plasmids, one of which expresses VEE glycoproteins and the other VEE capsid proteins, as described above, in order to obtain replicon particles.

In a further embodiment, the present invention relates to host cells stably transformed or transfected with the above-described recombinant DNA constructs. The host cell can be prokaryotic (for example, bacterial), lower eukaryotic (for example, yeast or insect) or higher eukaryotic (for example, all mammals, including but not limited to mouse and human). Both prokaryotic and eukaryotic host cells may be used for expression of desired coding sequences when appropriate control sequences which are compatible with the designated host are used. Among prokaryotic hosts, *E. coli* is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These markers may be used to obtain successful transformants by selection. Please see e.g., Maniatis, Fitsch and Sambrook, *Molecular Cloning; A Laboratory Manual* (1982) or *DNA Cloning,* Volumes I and II (D. N. Glover ed. 1985) for general cloning methods. The DNA sequence can be present in the vector operably linked to a sequence encoding an IgG molecule, an adjuvant, a carrier, or an agent for aid in purification of BoNT Hc proteins, such as glutathione S-transferase. The recombinant molecule can be suitable for transfecting eukaryotic cells, for example, mammalian cells and yeast cells in culture systems. *Saccharomyces cerevisiae, Saccharomyces carlsbergensis,* and *Pichia pastoris* are the most commonly used yeast hosts, and are convenient fungal hosts. Control sequences for yeast vectors are known in the art. Mammalian cell lines available as hosts for expression are known in the art and include many immortalized cell lines available from the American Type Culture Collection (ATCC), such as CHO cells, vero cells, and COS cells to name a few. Suitable promoters are also known in the art and include viral promoters such as that from SV40, Rous sarcoma virus (RSV), adenovirus (ADV), bovine papilloma virus (BPV), and cytomegalovirus (CMV). Mammalian cells may also require terminator sequences and poly A addition sequences; enhancer sequences which increase expression may also be included, and sequences which cause amplification of the gene may also be desirable. These sequences are known in the art.

The transformed or transfected host cells can be used as a source of DNA sequences described above. When the recombinant molecule takes the form of an expression system, the transformed or transfected cells can be used as a source of the protein or polypeptide cloned into the VEE replicon, or a source of RNA transcribed from the replicon as described above, or a source of replicon particles.

In a further embodiment, the present invention relates to a method of producing the recombinant or fusion protein which includes culturing the above-described host cells, under conditions such that the DNA fragment is expressed and the recombinant or fusion protein encoded by said DNA fragment is produced. The recombinant or fusion protein can then be isolated using methodology well known in the art. The recombinant or fusion protein can be used as a vaccine for immunizing against intoxication with BoNT or as a diagnostic tool for detection of botulism. The transformed host cells can be used to analyze the effectiveness of drugs and agents which inhibit toxin effects, such as host proteins or chemically derived agents or other proteins which may interact with the toxin to inibit its function. Increased or decreased botulinum toxicity can be measured using a mouse bioassay. The bioassay is normally used to determine whether serum antibodies, from any animal sources, can protect a naïve mouse from the effects of botulinum neurotoxin. The assay is performed by mixing a serum sample with active toxin which is then injected into a naïve mouse. If the mouse survives, then the serum sample contained protective, neutralizing antibodies. The assay could easliy be modified for testing anti-botulism drugs or agents. The drug or agent could be mixed with active toxin and then injected into a naïve mouse. If the mouse survives, then the drug or agent is effective at preventing botulism.

In another embodiment, the present invention relates to a botulinum neurotoxin vaccine comprising one or more replicon particles derived from one or more replicons encoding one or more BoNT Hc proteins or polypeptides as described above. The present invention also relates to a method for providing immunity against botulism said method comprising administering one or more replicon particles containing any combination of the BoNT proteins to a subject such that a protective immune reaction is generated.

Vaccine formulations of the present invention comprise an immunogenic amount of a replicon particle, resulting from one of the replicon constructs described above, or a combination of replicon particles as a multivalent vaccine, in combination with a pharmaceutically acceptable carrier. An "immunogenic amount" is an amount of the replicon particles sufficient to evoke an immune response in the subject to which the vaccine is administered. An amount of from about $10^2$ to $10^7$ per dose is suitable, more or less can be used depending upon the age and species of the subject being treated. Exemplary pharmaceutically acceptable carriers include, but are not limited to, sterile pyrogen-free water and sterile pyrogen-free physiological saline solution.

Administration of the replicon particles disclosed herein may be carried out by any suitable means, including both parenteral injection (such as intraperitoneal, subcutaneous, or intramuscular injection), by in ovo injection in birds, orally and by topical application of the virus (typically carried in the pharmaceutical formulation) to an airway surface. Topical application of the virus to an airway surface can be carried out by intranasal administration (e.g. by use of dropper, swab, or inhaler which deposits a pharmaceutical formulation intranasally). Topical application of the virus to an airway surface can also be carried out by inhalation administration, such as by creating respirable particles of a pharmaceutical formulation (including both solid particles and liquid particles) containing the replicon as an aerosol suspension, and then causing the subject to inhale the respirable particles. Methods and apparatus for administering respirable particles of pharmaceutical formulations are well known, and any conventional technique can be employed. An "immunogenic amount" is an amount of the replicon particles sufficient to evoke an immune response in the subject to which the vaccine is administered.

When the replicon RNA or DNA is used as a vaccine, the replicon RNA or DNA can be administered directly using techniques such as delivery on gold beads (gene gun), delivery by liposomes, or direct injection, among other methods known to people in the art. Any one or more constructs or replicating RNA described above can be use in any combination effective to elicit an immunogenic response in a subject. Generally, the nucleic acid vaccine administered may be in an amount of about 1–5 ug of nucleic acid per dose and will depend on the subject to be treated, capacity of the subject's immune system to develop the desired immune response, and the degree of protection desired. Precise amounts of the vaccine to be administered may depend on the judgement of the practitioner and may be peculiar to each subject and antigen.

The vaccine may be given in a single dose schedule, or preferably a multiple dose schedule in which a primary course of vaccination may be with 1–10 separate doses, followed by other doses given at subsequent time intervals required to maintain and or reinforce the immune response, for example, at 1–4 months for a second dose, and if needed, a subsequent dose(s) after several months. Examples of suitable immunization schedules include: (i) 0, 1 months and 6 months, (ii) 0, 7 days and 1 month, (iii) 0 and 1 month, (iv) 0 and 6 months, or other schedules sufficient to elicit the desired immune responses expected to confer protective immunity, or reduce disease symptoms, or reduce severity of disease.

The following MATERIALS AND METHODS were used in the examples that follow.

Plasmids.

Construction of the VEE replicon, capsid (C-) helper, and glycoprotein (GP-) helper plasmids was previously described (Pushko, 1997, supra). The Hc gene (Clayton, 1995, supra) was cloned into the VEE replicon plasmid as a XhoI/Hind III fragment utilizing a shuttle vector. The Lassa nucleocapsid replicon (Lassa N-replicon) was constructed as previously described (Pushko 1997, supra) and used as a negative control replicon.

Replicon p3014-40A was cloned as follows: The BoNT/A Hc gene was cut out of pMutAC-1 (obtained from Clayton et al., 1995, supra) with Xho I and Hind III. The gene was ligated into pALTER-1 (Promega, Inc.) at a compatible Sal I and a Hind III site. The BoNT/A Hc gene was cut out of pALTER/Hc with Xba I (the site was located just upstream of the Sal I site) and Hind III. The gene was ligated into the KS2 Shuttle vector, cut out with Apa I and Not I, and ligated into the replicon pVR2 (Drawing sheet 1, U.S. Pat. No. 5,792,462 to Johnston et al.).

Replicons p3014-115a1 and -102a2 were cloned as follows: The BoNT/A subHc a1 and a2 genes were PCR amplified from p3014-40A using forward primers containing a 5' Cla I recognition site, a start codon, and complimentary to the 5' end of the subgenes, from nucleotide 9 to 28 for a1 and from nucleotide 708 to 731 for a2, and reverse primers containing a 3' Cla I recognition site, a stop codon, and complimentary to the 3' end of the subgenes, from nucleotide 686 to 707 for a1 and from nucleotide 1305 to 1325 for a2 (numbering according to Clayton et al., 1995, supra). The PCR products were gel purified and then ligated into pCR2.1(Invitrogen, Inc.). The genes were cut out of pCR-suba1 or pCR-suba2 with Cla I and ligated into pVR2 replicon.

Replicon 3014-73B, -110C, -75E, -77F, and -107G were cloned as follows: An EcoRI digest of plasmids pBoNT/B (Hc), pBoNT/C(Hc), pBoNT/E(Hc), pBoNT/F(Hc), and pBoNT/G(Hc) resulted in an EcoRI DNA fragment containing Hc fragments of serotypes B, C, E, F, and G, respectively. The EcoRI fragments were each ligated into the KS2 Shuttle. The orientation of each gene was determined and then the genes were cut out of the shuttle with Apa I and Not I. The Apa I/Not I genes were ligated into the pVR2 replicon.

Production of VRP. Plasmid templates for the Hc-replicon, C-helper, GP-helper, and the Lassa N-replicon were linearized by digestion with NotI at a unique site downstream from the coding sequences, and capped run-off transcripts were prepared in vitro using T7 RNA polymerase. Packaging of the replicons into VEE replicon particles (VRPs) was accomplished by electroporating the replicon RNA and the two helper RNAs into BHK cells. VRPs were harvested between 20 and 27 hours after transfection and purified from cell culture supernatants by ultracentrifugation through a discontinuous sucrose gradient (20%). After reconstituting the pelleted VRP in 1/50 volume phosphate buffered saline, the VRPs were stored at −70° C.

Analysis of Expression Products and Titration of VRP

Subconfluent monolayers were infected with Hc-VRP or Lassa N-VRP (m.o.i.=2) or cell suspensions were electroporated with replicon RNA. Cells were harvested at approximately 20–24 hours and expressed proteins were separated by SDS-PAGE. Visualization of Hc protein (50 kDa) was accomplished using a chemiluminescence western blot assay and antibodies specific for each protein. Titration of VRPs was accomplished by infecting subconfluent monolayers with increasing dilutions of purified VRP. Antigen positive cells were visualized in an indirect immunofluorescence assay using a monoclonal antibody specific for each protein, or in a direct immunofluorescence assay using an FITC-conjugated monkey anti-Lassa serum.

Immunization of Mice.

Mice were inoculated 1 to 4 times at 7 to 28 day intervals with $10^5$ to $10^7$ infectious units (iu) of either Hc-VRP or Lassa N-VRP (negative control). Positive control mice for the botulinum study were inoculated subcutaneously with 0.2 ml of human botulinum vaccine at 28 day intervals. Serum for ELISA was obtained 2 days before each inoculation and 3 days before challenge.

For the duration of immunity challenge, the mice were challenged intraperitoneally with $10^3$ $LD_{50}$ units of BoNT/A in 0.2% gelatin/PBS 24 weeks after the last inoculation. Swiss mice were challenged intraperitoneally with $10^3$ LD50 units of BoNT/B in 0.2% gelatin/PBS 31 days after the last inoculation.

Enzyme-linked Immunosorbent Assay (ELISA)

Microtiter plates were coated with botulinum neurotoxin (1 ug/ml) in PBS and allowed to absorb overnight at 4° C. Four fold serum dilutions in blocking buffer were applied to the plates and incubated at 37° C. for 1 hour. After washing, an anti-mouse secondary antibody (HRP conjugated) was added to the plate and incubated for an additional hour at 37° C. After washing, bound antibody was detected colormetrically using ABTS as a substrate.

Challenge of Mice.

Botulinum neurotoxin challenge: Balb/c and Swiss mice were challenged intraperitoneally with $10^2$ to $10^5$ $LD_{50}$ units of BoNT/A in 0.2% gelatin/PBS 31 days after the last inoculation.

EXAMPLE 1

Packaging and Expression of Hc-replicon

The Hc-replicons were efficiently packaged into VRPs using the double helper system. Stock solutions contained about $10^8$ iu of purified VRP per milliliter. No replication competent VEE virus was detected in any of the preparations using a standard plaque assay. Cells infected with VRP or transfected with replicons encoding Hc expressed high levels of these proteins as demonstrated by western blot (FIG. 1) and by immunofluorescence. VEE replicons expressing the above genes produced proteins that comigrated on gels with authentic proteins and reacted efficiently with antibodies raised to the authentic proteins.

EXAMPLE 2

Protection Against Challenge with BoNT.

Results from animal studies demonstrated that the VEE replicon expressing the 50-kDa carboxy-terminal fragment of botulinum neurotoxin (Hc) type A or type B polypeptide could immunize and protect mice from a lethal challenge of BoNT/A or BoNT/B, respectively. Balb/c mice inoculation with Hc-VRP (serotype A) at day 0 produced a maximum antibody response around day 19 which remained constant to at least day 26 (FIG. 2). Booster inoculations given at day 7, 14, 21, or 28 stimulated a good secondary antibody response. If both doses of the Hc-VRP were given on the same day, the primary antibody response was 2.96 logs (serum was obtained 28 days post inoculation) as compared to 1.73 logs for mice that received 2 doses of the Lassa N-VRP (Lassa N-VRP was given at day 0 and 28; serum was obtained 28 days post-second inoculation). Even though the mice that received 2 doses of Hc-VRP on day 0 were not protected from challenge, the time to death was increased from 6 hours (for mice that received the Lassa N-VRP) to 33 hours. Mice that received a booster inoculation on day 7 produced a secondary antibody response of 3.23 logs with 8 out of 10 surviving challenge with 1000 $LD_{50}$ units of BoNT/A. Mice that received booster inoculations on day 14, 21, or 28 produced higher secondary antibody responses of 3.87, 4.44, and 4.56 logs, respectively, with all mice surviving challenge with 1000 $LD_{50}$ units of BoNT/A. Thus, the most beneficial inoculation schedule was 2 doses of Hc-VRP given at least 21 days apart.

Figure 3:
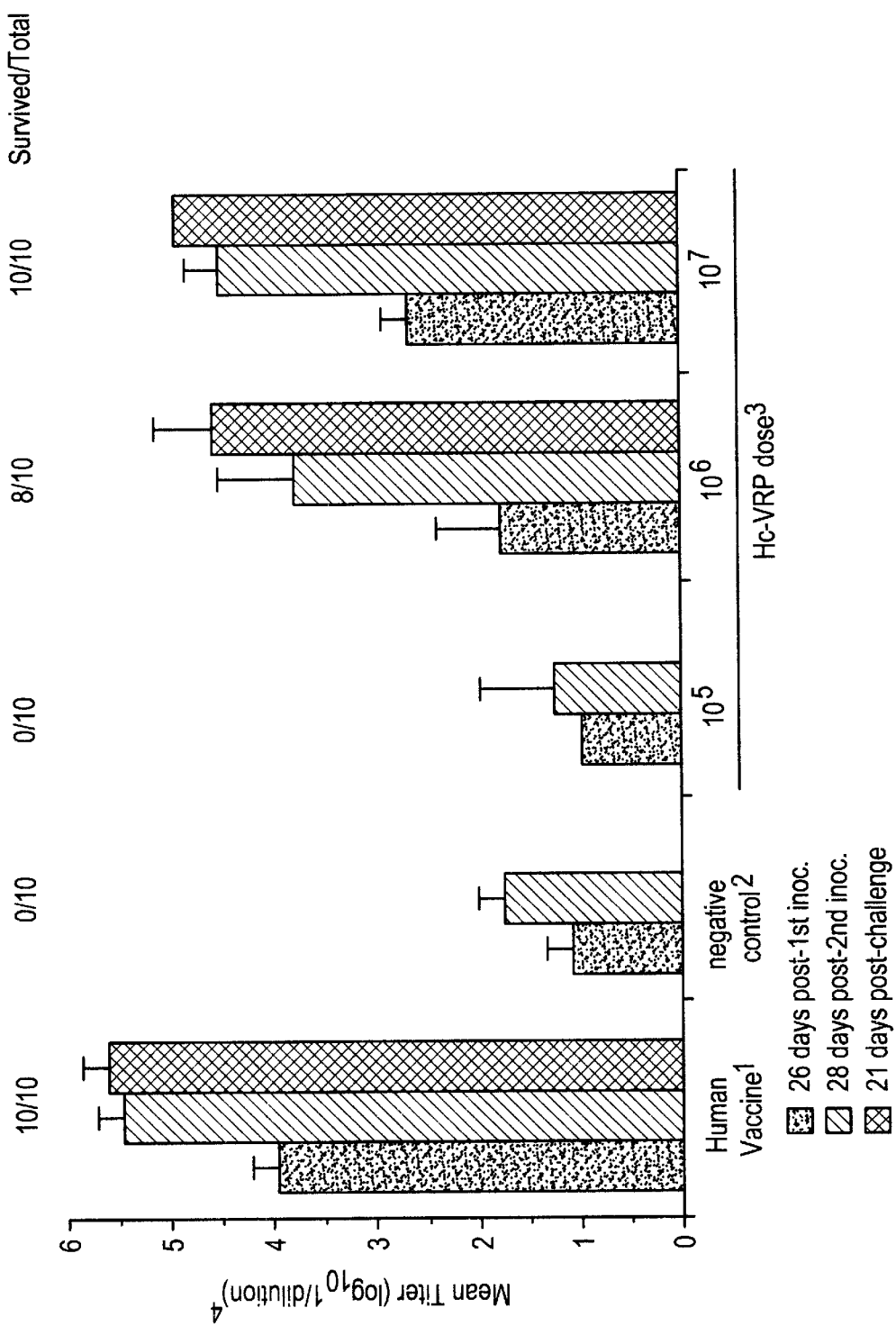
FIG. 3. ELISA titers for Balb/c mice immunized with varying amounts of Hc-VRP. 1) 0.2 ml human vaccine given at day 0 and 28; 2) $10^7$ iu Lassa N-VRP given at day 0 and 28; 3) Hc-VRP inoculation given at day 0 and 28; 4) Titers less than 2 logs or greater than 5.61 logs were estimated. Challenge was 31 days after last inoculation with 1000 $LD_{50}$ BoNT/A.

FIG. 3 shows the ELISA titers and survival for BALB/c mice inoculated with doses of Hc-VRP ranging from $10^5$ to $10^7$ iu. The dose of Hc-VRP (given twice at an interval of 28 days) required to completely protect BALB/c mice from a lethal challenge of 1000 $LD_{50}$ BoNT/A was between $10^6$ and $10^7$ iu. The pre-challenge serum ELISA titers from BALB/c mice immunized with $10^5$, $10^6$ or $10^7$ iu of Hc-VRP was 1.27, 3.81, and 4.56 logs, respectively, as compared to 1.73 logs for mice that received the negative control replicon. None of the animals inoculated with $10^5$ iu of Hc-VRP or the negative control replicon survived challenge whereas 8 of 10 and 10 of 10 mice that received $10^6$ or $10^7$ iu of Hc-VRP survived challenge. Table 2 shows a comparison of data obtained from animals challenge with 100 to 100,000 $LD_{50}$ units of BoNT/A. Two inoculations of $10^7$ iu of Hc-VRP protected 90% of the BALB/c mice from a lethal challenge of 100,000 $LD_{50}$ units of BoNT/A.

Figure 4:
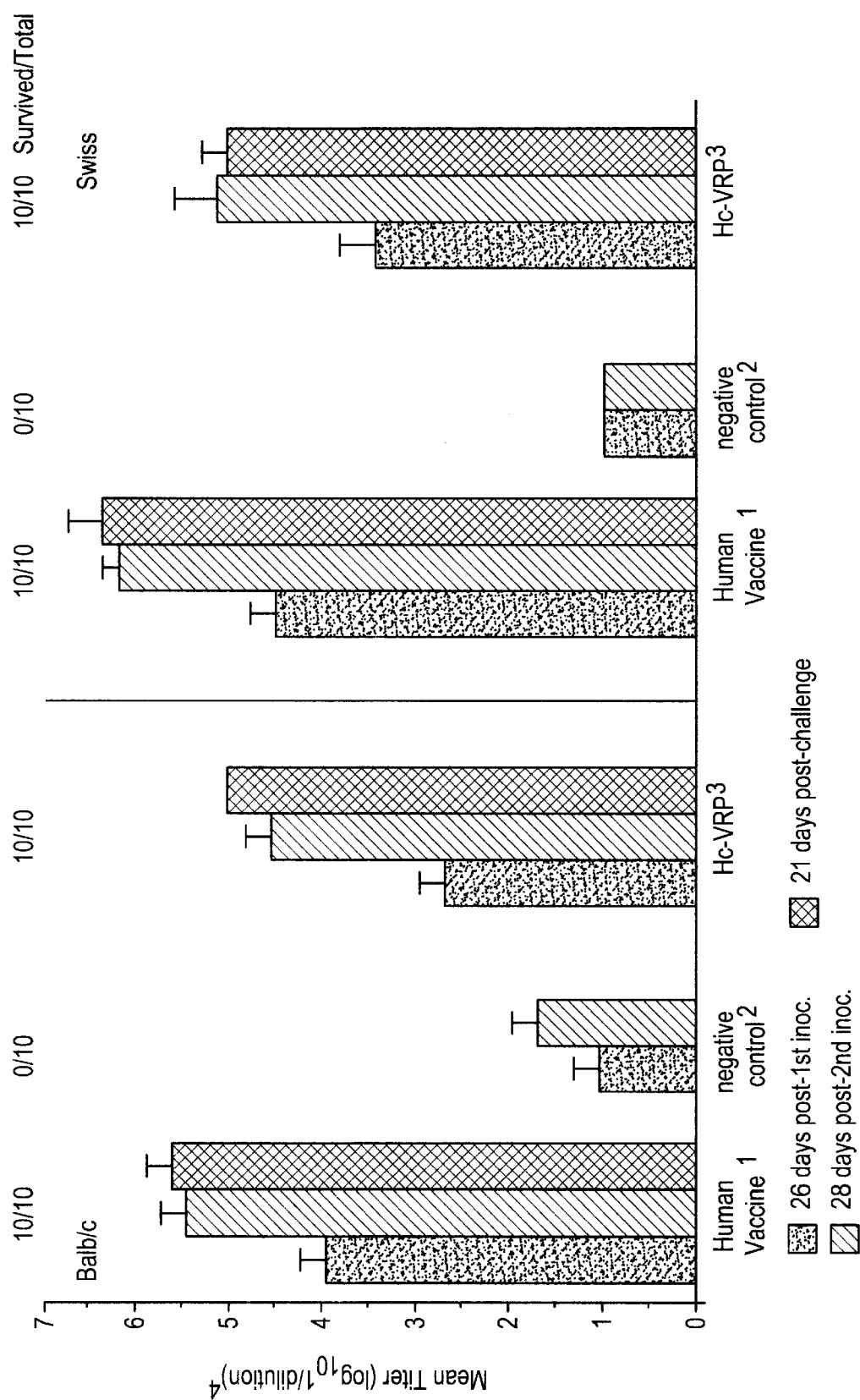
FIG. 4. ELISA titers for Balb/c and Swiss mice immunized with Hc-VRP. 1) 0.2 ml human vaccine given at day 0 and 28; 2) $10^7$ iu Lassa N-VRP given at day 0 and 28; 3) $10^7$ iu Hc-VRP given at day 0 and 28; 4) Titers less than 2 logs or greater than 5.61 logs were estimated. Challenge was 31 days after last inoculation with 1000 $LD_{50}$ BoNT/A.
Figure 5:
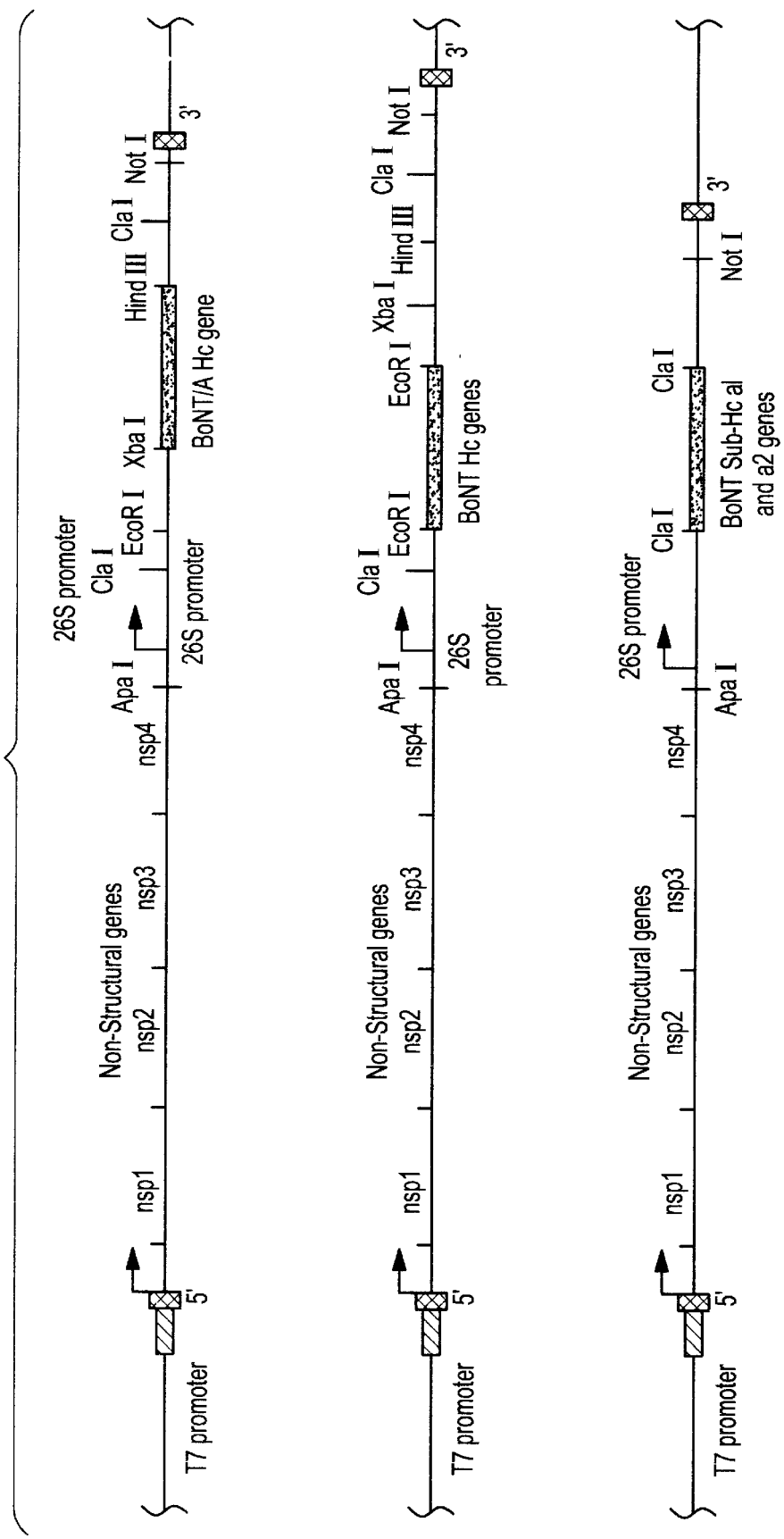
FIG. 5. Schematic of constructs containing BoNT/Hc fragments.

FIG. 4 shows ELISA titers and survival for Swiss mice inoculated with Hc-VRP. Two doses of $10^7$ iu Hc-VRP protected 100% of the mice from an otherwise lethal challenge of 1000 $LD_{50}$ units of BoNT/A. The protection achieved in the SWISS mice demonstrated the ability of the Hc-replicon to protect outbred animals. The geometric mean titer from SWISS mice immunized with the Hc-VRP was 5.13 logs as compared to 1 log for mice that received the negative control replicon. None of the animals inoculated with the negative control replicon survived challenge.

TABLE 2

BoNT/A Hc replicon protects Balb/c mice from challenge.

| Replicon Dose (ffu)[1] | ELISA GMT[2] | Challenge Dose (LD50)[3] | Survived/Total[4] |
|---|---|---|---|
| $10^7$ | 67558 | $10^2$ | 10/10 |
| $10^7$ | 51200 | $10^3$ | 10/10 |
| $10^7$ | 75250 | $10^4$ | 9/10 |
| $10^7$ | 87781 | $10^5$ | 9/10 |

[1]Replicon inoculated at day 0 and 28; ffu, fucus forming units.
[2]Prechallenge end point titers.
[3]Challenge was 28 days after the last inoculation with the above LD50 BoNT/A.
[4]Mice that died, titer = 100; 102400

Swiss mice inoculation with different amounts of Hc-VRP (serotype B) at day 0 and day 28 were partially to fully protected from challenge. Two doses of $10^6$ Hc-VRP only protected 3 out of 10 mice whereas two doses of $10^7$ Hc-VRP protected 10 out of 10 mice from a 1000 $LD_{50}$ BoNT/B challenge.

Swiss mice inoculted with Hc-VRP (serotype E) were not protected from challenge. Some modifications of the gene, either shortening or adding some sequences (from the N-terminal part of the Heavy Chain) may help increase protection with Hc-VRP (serotype E).

Swiss mice inoculation with different amounts of Hc-VRP (serotype F) at day 0 and day 28 were partially protected from challenge. Two doses of 10 Hc-VRP only protected 1 out of 10 mice whereas two doses of $10^7$ Hc-VRP protected 3 out of 10 mice from a 1000 $LD_{50}$ BoNT/F challenge.

The Hc-replicon's ability to induce long term immunity was investigated by inoculating mice with Hc-VRP (serotype A) and then challenging 6 months post vaccination. Swiss mice were inoculated with either $10^6$ or $10^7$ Hc-VRP at week 0 and 4 and then challenged during week 28. Mice that received $10^6$ Hc-VRP were almost fully protected, 9 out of 10 survived, while mice that received $10^7$ Hc-VRP were completely protected, 10 out of 10 survived, from a 1000 $LD_{50}$ BoNT/A challenge.

The ability of Hc-VRP (serotypes E, C and D) to protect animals from challenge with these toxins is being investigated.

EXAMPLE 3

Immunogenicity and efficacy of replicons, expressing either the native or synthetic gene fragments of the heavy chain of BoNT/A, and the botulinum toxoid vaccine were compared. VEE replicon vector containing native sequences encoding the BoNT/A heavy chain N fragment (BoNT/A HN), the BoNT/A heavy chain C fragment (BoNT/A HC), the BoNT/A heavy chain (BoNT/A H), and a synthetically derived sequence encoding the BoNT/A heavy chain C fragment (synBoNT/A Hc) (Clayton et al., 1995, supra) were used in this experiment.

After production of VRPs as described above, Swiss mice were inoculated subcutaneously on days 0, 38, and 56 with $10^5$, $10^6$, or $10^7$ VRPs either expressing BoNT/A $H_N$, BoNT/A $H_C$, or BoNT/A H; all encoded by their respective native gene sequences. Another group of mice received $10^7$ VRPs expressing synBoNT/A Hc. For a negative control, mice were immunized with $10^7$ VRPs expressing the Lassa virus nucleocapsid replicon (Lassa N-Rep), and for a positive control, mice were immunized with 0.2 ml of the current human BoNt toxoid vaccine (pentavalent, A-E, formaldehyde-inactivated vaccine with adjuvant). Before each inoculation, the mice were retro-orbitally bled, and sera was isolated on days 23, 51, and 79. Antibody (Ab) titers to BoNT/A were determined on each serum sample using ELISA. Purified BoNT/A was used as ELISA antigen. On day 84, each mouse was challenged intraperitoneally with 1000 $LD_{50}$ of BoNT/A. The mice were then examined daily for 7 days after challenge to determine if protection was conferred.

Mice immunized with either the toxoid vaccine or $10^7$ VRPs expressing the synthetic BoNT/A Hc (synBoNT/A Hc) were completely protected from challenge while mice inoculated with $10^7$ VRPs expressing the native BoNT/A $H_C$ were almost completely protected (16 of 20 mice survived challenge) (see table 3). In addition, partial protection was observed in mice immunized with $10^6$ VRPs expressing the native BoNT/A Hc (9 of 19 mice survived challenge).

TABLE 3

Survival and ELISA titers of Swiss mice inoculated with different immunogens and challenged with BoNT/A

| Immunogen | Gene Sequence | Dose | Survivors/ total | Pre-challenge GMT[b] ($\log_{10}$) | MDD[a] |
|---|---|---|---|---|---|
| synBoNT/A Hc replicon | Synthetic | $10^7$ | 18/18 | 5.25 | — |
| Toxoid vaccine | n/a | 0.2 ml | 20/20 | 6.07 | — |
| Lassa N replicon | n/a | $10^7$ | 0/20 | 1.65 | 1 |
| BoNT/A Hn replicon | Native | $10^3$ | 0/20 | 1.43 | 1 |
| BoNT/A Hn replicon | Native | $10^6$ | 0/18 | 2.05 | 1 |
| BoNT/A Hn replicon | Native | $10^7$ | 0/20 | 2.68 | 1 |
| BoNT/A Hc replicon | Native | $10^5$ | 1/20 | 1.88 | 1 |
| BoNT/A Hc replicon | Native | $10^6$ | 9/19[a] | 3.63 | 1 |
| BoNT/A Hc replicon | Native | $10^7$ | 16/20 | 5.19 | 1 |
| BoNT/A H replicon | Native | $10^5$ | 0/20 | 1.66 | 1 |
| BoNT/A H replicon | Native | $10^6$ | 0/20 | 2.10 | 1 |
| BoNT/A H replicon | Native | $10^7$ | 0/20 | 2.82 | 1 |

Mice were intraperitoneally challenged with 1000 LD50 BoNT/A.
[a]Mice died during retro-orbital bleed;
[b]GMT, geometric mean titer determined on serum obtained 5 days prior to challenge;
MDD, mean day to death for those mice that failed to survive challenge Discussion/Conclusion Since VEE virus replicates in the cytoplasm of eukaryotic cells, the VEE replicon vaccine vector is a useful tool for the expression of prokaryotic genes in eukaryotic cells. Cytoplasmic expression of genes alleviates the difficulties imposed by splicing and nuclear transport of mRNA. We used the VEE replicon as a way to express the prokaryotic Hc genes in eukaryotic cells and to develop new vaccine candidates against botulinum neurotoxin.

Development of a new candidate vaccine against botulinum neurotoxin would overcome problems associated with the current human vaccine. The current vaccine requires 4 inoculations over 12 months and only protects against 5 of the 7 serotypes. High production costs and high reactogenicity (up to 20% of the recipients developed mild to moderate local reaction after receiving booster inoculations) are just two other problems associated with the current vaccine. We constructed new candidate vaccines, the Hc-replicon vaccines, that may overcome these problems.

Hc-replicons produced large amounts of protein in vitro, as determined by western blot analysis of cell lysates and by immunofluorescence of fixed cells, and elicited a good immune response when inoculated into mice. We found that two inoculations of Hc-VRP (serotype A) given on day 0 and 21 or 28 produced the strongest secondary antibody response and protected mice from the effects of botulinum neurotoxin serotype A. Mice inoculated with Hc-VRP (serotype B) were similarly protected from challenge; complete protection was observed using a homologous challenge of BoNT/B. Mice that received 2 inoculation of Hc-VRP (serotype A) were also protected against 100,000 $LD_{50}$ units of BoNT/A, an extremely high challenge dose. The Hc-replicon was also able to induce long term protection in mice; with protection lasting for at least 6 months. The Hc-replicon vaccines, using the synthetic or native sequence of the heavy chain, were effective in blocking the effects of botulinum neurotoxin and may alleviate most of the problems associated with the current vaccine.

What is claimed is:

1. A recombinant DNA construct comprising:
   (i) a vector VEE, and
   (ii) at least one nucleic acid fragment comprising a carboxy terminal heavy chain fragment from any of BoNTA, BoNTB, BoNTC, BoNTD, BoNTE, BoNTF, and BoNTG.

2. A recombinant DNA construct according to claim 1 wherein said vector is an expression vector.

3. A recombinant DNA construct according to claim 1 wherein said vector further comprises a prokaryotic vector.

4. A recombinant DNA construct according to claim 1 wherein said vector further comprises another eukaryotic vector.

5. The recombinant DNA construct according to claim 1 wherein said construct is p3014-40A.

6. The recombinant DNA construct according to claim 1 wherein said construct is p3014-114a1.

7. The recombinant DNA construct according to claim 1 wherein said construct is p3014-102a1.

8. The recombinant DNA construct according to claim 1 wherein said construct is p3014-73B.

9. The recombinant DNA construct according to claim 1 wherein said construct is p3014-110C.

10. The recombinant DNA construct according to claim 1 wherein said construct is p3014-75E.

11. The recombinant DNA construct according to claim 1 wherein said construct is p3014-77F.

12. The recombinant DNA construct according to claim 1 wherein said construct is p3014-107G.

13. A host cell transformed with a recombinant DNA construct according to claim 1.

14. A host cell transformed with a recombinant DNA construct according to claim 3.

15. A host cell transformed with a recombinant DNA construct according to claim 4.

16. A method for producing BoNT Hc protein comprising culturing the cells according to claim 13 under conditions such that said DNA fragment is expressed and said protein is produced.

17. Self replicating VEE RNA produced from any of the constructs chosen from the group consisting of: p3014-40a, p3014-114a1, p3014-102a2, p3014-73B, p3014-110C, p3014-75E, p3014-77F, and p3014-107G.

18. Infectious VEE particles produced from packaging the self replicating RNA of claim 17.

19. A pharmaceutical composition comprising infectious alphavirus particles according to claim 18 in an effective immunogenic amount in a pharmaceutically acceptable carrier and/or adjuvant.

20. A pharmaceutical composition comprising the self replication RNA of claim 17 packaged in VEE particle in an effective immunogenic amount in a pharmaceutically acceptable carrier and/or adjuvant.

21. A pharmaceutically composition comprising a pharmaceutically acceptable carrier and/or adjuvant and an RNA or DNA construct in a pharmaceutically acceptable amount, wherein the RNA or DNA construct produces a self-replicating VEE RNA containing the same BoNT insert as p3014-40a, p3014-114a, p3014-102a, p3014-73B, p3014-110C, p3014-75E, p3014-77F, or p3014-107G.

22. A vaccine for BoNTA comprising VEE viral particles containing one or more replicon RNA encoding one or more BoNTA proteins and, optionally one or more antigens selected from the group consisting of HcBoNTB, HcBoNTC, HcBoNTD, HcBoNTE, HcBoNTF, and HcBoNTG.

23. A vaccine for BoNTB comprising VEE viral particles containing one or more VEE replicon RNA encoding one or more BoNTB proteins and, optionally, one or more antigens selected from the group consisting of HcBoNTA, HcBoNTC, HcBoNTD, HcBoNTE, HcBoNTF, and HcBoNTG.

24. A vaccine for BoNTC comprising VEE viral particles containing one or more VEE replicon RNA encoding one or more BoNTC proteins and, optionally, one or more antigens selected from the group consisting of HcBoNTA, HcBoNTB, HcBoNTD, HcBoNTE, HcBoNTF, and HcBoNTG.

25. A vaccine for BoNTD comprising VEE viral particles containing one or more replicon RNA encoding one or more BoNTD proteins and, optionally, one or more antigens selected from the group consisting of HcBoNTA, HcBoNTB, HcBoNTC, HcBoNTE, HcBoNTF, and HcBoNTG.

26. A vaccine for BoNTE comprising VEE viral particles containing one or more VEE replicon RNA encoding one or more BoNTE proteins and, optionally, one or more antigens selected from the group consisting of HcBoNTA, HcBoNTB, HcBoNTC, HcBoNTD, HcBoNTF, and HcBoNTG.

27. A vaccine for BoNTF comprising VEE viral particles containing one or more VEE replicon RNA encoding one or more BoNTF proteins and, optionally, one or more antigens selected from the group consisting of HcBoNTA, HcBoNTB, HcBoNTC, HcBoNTD, HcBoNTE, and HcBoNTG.

28. A vaccine for BoNTG comprising VEE viral particles containing one or more VEE replicon RNA encoding one or more BoNTG proteins and, optionally, one or more antigens selected from the group consisting of HcBoNTA, HcBoNTB, HcBoNTC, HcBoNTD, HcBoNTE, and HcBoNTF.

* * * * *